(12) United States Patent
Haas

(10) Patent No.: US 6,428,472 B1
(45) Date of Patent: Aug. 6, 2002

(54) SURGICAL RETRACTOR HAVING A MALLEABLE SUPPORT

(76) Inventor: Kent Haas, 2009 Stone Ridge La., Villanova, PA (US) 19085

( * ) Notice: Subject to any disclaimer, the term of this patent is extended or adjusted under 35 U.S.C. 154(b) by 0 days.

(21) Appl. No.: 09/634,534

(22) Filed: Aug. 8, 2000

(51) Int. Cl.[7] .................................................. A61B 1/32
(52) U.S. Cl. ........................ 600/206; 600/213; 600/226
(58) Field of Search ................................. 600/206, 213, 600/226, 227, 231, 201, 235

(56) References Cited

U.S. PATENT DOCUMENTS

| | | | |
|---|---|---|---|
| 3,882,855 A | | 5/1975 | Schulte et al. |
| 4,048,987 A | * | 9/1977 | Hurson .................... 600/233 X |
| 4,226,228 A | | 10/1980 | Shin et al. |
| 4,239,036 A | | 12/1980 | Krieger |
| 4,421,107 A | | 12/1983 | Estes et al. |
| 4,610,243 A | | 9/1986 | Ray |
| 4,616,633 A | | 10/1986 | Vargas Garcia |
| 4,738,248 A | * | 4/1988 | Ray ........................... 600/206 |
| 4,889,107 A | | 12/1989 | Kaufman |
| 5,971,920 A | * | 10/1999 | Nagel ......................... 600/206 |

OTHER PUBLICATIONS

Miltex Surgical Instruments/Catalog (1986).

* cited by examiner

Primary Examiner—Jeffrey A. Smith

(57) ABSTRACT

A retractor device for use in surgical procedures is disclosed. The retractor has a handle element that is held by a surgeon. The handle element has a first end and a second end. At least a portion of the handle element between the first end and the second end is fabricated from a malleable material. The malleable material enables the relative position between the first end of the handle element and the second end of the handle element to be selectively adjusted by hand. A rigid retractor blade extends from the first end of the handle element. By altering the shape of the handle element, the orientation of the rigid retractor blade can be selectively altered. As such, a surgeon can selectively change the shape of the retractor without sacrificing the strength of the contact blade portion of the retractor.

9 Claims, 5 Drawing Sheets

SURGICAL RETRACTOR HAVING A MALLEABLE SUPPORT

BACKGROUND OF THE INVENTION

1. Field of the Invention

In general, the present invention relates to retractors that are used to manipulate and retain tissue during a surgical procedure. More particularly, the present invention relates to the structure and composition of surgical retractors.

2. Description of the Prior Art

When a patient undergoes intrusive surgery, a surgeon makes an incision in the skin to approach the tissue that requires repair or removal. As is often the case, the body tissue needing repair or removal is seldom just below the skin. Rather, a surgeon must often approach tissue that is positioned below a myriad of veins, arteries, bones, muscles and internal organs. In order to expose an area of targeted tissue deep within the body, surgeons use retractors to manipulate interposing tissue and hold that interposing tissue out of the way. In this manner, a clear surgical opening can be created to the targeted tissue, thereby enabling a surgeon to observe and repair, or remove, the targeted tissue.

Many surgical procedures are standardized. For example, during open heart surgery, the heart is approached through the sternum. In many such operations, a surgeon knows what tissue lay between the skin and the targeted tissue. As such, the surgeon has a variety of different retractors available that are used to manipulate and retain the interposing tissue. Each of the retractors has a particular shape that is appropriate for manipulating or retaining the interposing material that will be encountered.

Since surgeons can anticipate the type of interposing tissue that will be encountered in different types of surgical procedures, retractors are manufactured in a variety of different configurations in order to be useful for the different surgical procedures. For example, there are retractors specifically designed for use in open heart surgeries. There are retractors specifically designed for use in gall bladder surgeries, and there are retractors specifically designed for use in appendectomy surgeries. The number of specialized standard retractors nearly mimics the number of specialized standard surgical procedures.

Most specialized retractors are made of stainless steel and are rigid. The shape of the retractor is predetermined in view of its intended use. Such retractors are made in different sizes in order to accommodate patients of different sizes and the particular preferences of the surgeon.

Hundreds of different types of surgical retractors exist. Obviously, when a surgical team operates, all of the existing retractors are not provided in the operating room. Rather, prior to the operation, the surgical team selects the retractors that their experience tells them they will most probably need. A problem occurs when the surgical team encounters a mass of interposing tissue that was not fully anticipated. This is not uncommon because no two people are anatomically identical. In such circumstances, the surgical team must improvise and use a retractor that is not quite appropriate for the job at hand.

In an attempt to make improvisation a little less difficult, malleable ribbon retractors have been developed. Malleable ribbon retractors are retractors that are long, thin and flat. The retractors are made from malleable material that can be custom bent into most any desired shape during the surgery. As such, surgeons can be assured that they can adapt the malleable retractor to their needs during the surgery.

Although malleable ribbon retractors are more versatile than are rigid stainless steel retractors, they do have certain disadvantages. One of those disadvantages is strength. Rigid stainless steel retractors are very strong. As such, a surgeon can apply a lot of pressure to those instruments in order to move bone, muscle or other dense tissue. Malleable ribbon retractors are malleable. Thus, they are incapable of transferring strong forces to body tissue without deforming in shape as a result of those forces.

A need therefore exists for an improved retractor that has the strength of a solid stainless steel retractor yet has the versatility of a malleable retractor. This need is met by the present invention as described and claimed below.

SUMMARY OF THE INVENTION

The present invention is a retractor device for use in surgical procedures. The retractor has a handle element that is held by a surgeon. The handle element has a first end and a second end. At least a portion of the handle element between the first end and the second end is fabricated from a malleable material. The malleable material enables the relative position between the first end of the handle element and the second end of the handle element to be selectively adjusted by hand.

A rigid retractor blade extends from the first end of the handle element. The retractor blade is used to contact and manipulate tissue within the body. By altering the shape of the handle element, the orientation of the rigid retractor blade can be selectively altered. As such, a surgeon can selectively change the shape of the retractor without sacrificing the strength of the contact blade portion of the retractor.

BRIEF DESCRIPTION OF THE DRAWINGS

For a better understanding of the present invention, reference is made to the following description of an exemplary embodiment thereof, considered in conjunction with the accompanying drawings, in which.

DETAILED DESCRIPTION OF THE INVENTION

Figure 1:
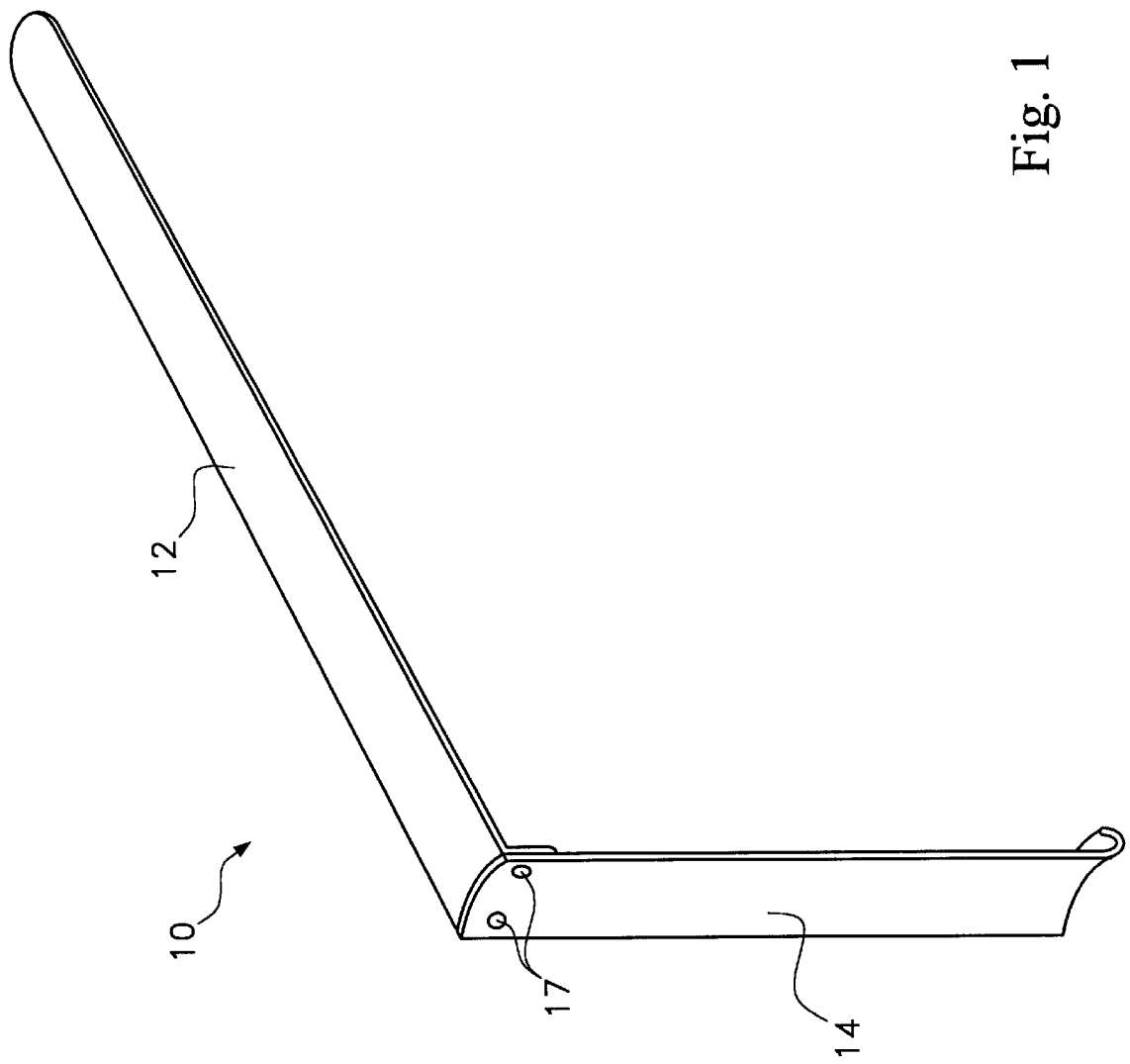
FIG. 1 is a perspective view of an exemplary embodiment of a surgical retractor device in accordance with the present invention.
Figure 2:
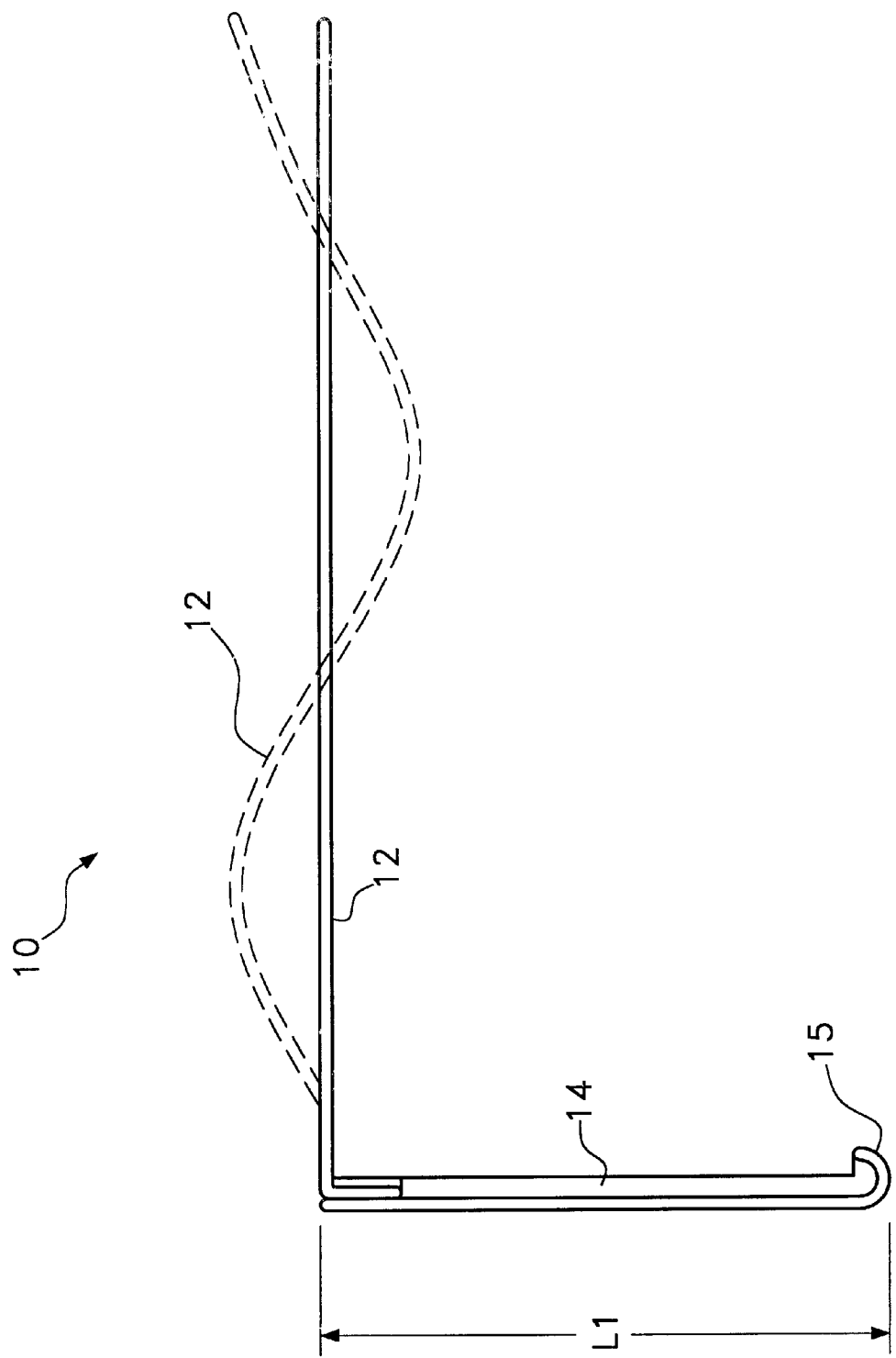
FIG. 2 is side view of the embodiment of FIG. 1.

Referring to FIG. 1 in conjunction with FIG. 2, an exemplary embodiment of a retractor 10 is illustrated in accordance with the present invention. The retractor 10 is a hand-held retractor to be used by a surgeon during an intrusive surgical procedure. The retractor 10 is comprised of a handle element 12 and a blade element 14 that extends from one end of the handle element 12 near or at a perpendicular.

The blade element 14 of the retractor 10 is made of stainless steel or another appropriate rigid, non-corrosive metal. The blade element 14 of the retractor 10 has a length L1 (FIG. 2), which can be anywhere from one half inch to eight inches in length. The blade element 14 of the retractor is straight, yet is indented into a semi-cylindrical shape. The bottom end 15 of the blade element 14 is curved back toward the direction of the handle element 12. The curved shape of the blade element 14, along with its stainless steel construction, provides the blade element 14 with great strength and rigidity. Accordingly, any manual forces applied to the retractor 10 will do little to deform the prefabricated form of the retractor's blade element 14.

The handle element 12 of the retractor 10 is made of malleable material. The malleable material can be any alloy composition currently used in the manufacture of prior art malleable retractors. The alloy and dimensions used in the handle element 12 are selected so that a surgeon can deform the handle element 12 using his/her hands during an operation.

The malleable handle element 12 of the retractor 10 is joined to the rigid blade element 14 through a heat weld and/or the use of mechanical fasteners 17 (FIG. 1).

By having a retractor 10 with a rigid blade element 14 and a malleable handle element 12, a retractor 10 is provided that is very strong where it counts, yet is highly versatile. To use the retractor 10, the handle element 12 is manually deformed so as to position the rigid blade element 14 where it is needed during a surgical procedure. The deformation of the handle element 12 is shown with hidden lines in FIG. 2. The rigid blade element 14 itself is the part of the retractor 10 that contacts tissue within the body. As a result, the direct force of the retractor 10 against the body is experienced by the rigid blade element 14. The handle element 12 of the retractor 10 mainly experiences tension as a surgeon pulls on the handle element 12 to bias the blade element 14 against tissue in the body. Due to the elongated shape of the retractor's handle element 12, the handle element 12 is relatively resistant to deformation when tensile forces are applied, but is not resistant to deformation when lateral bending forces are applied. Accordingly, a surgeon can easily bend the handle element 12 when desired. However, significant tensile forces can be transferred through the handle element 12 to the blade element 14 without the handle element 12 deforming. The result is a retractor 10 that can be shaped as desired by a surgeon, yet will not deform from that selected shape when used by the surgeon during an operation.

Figure 3:
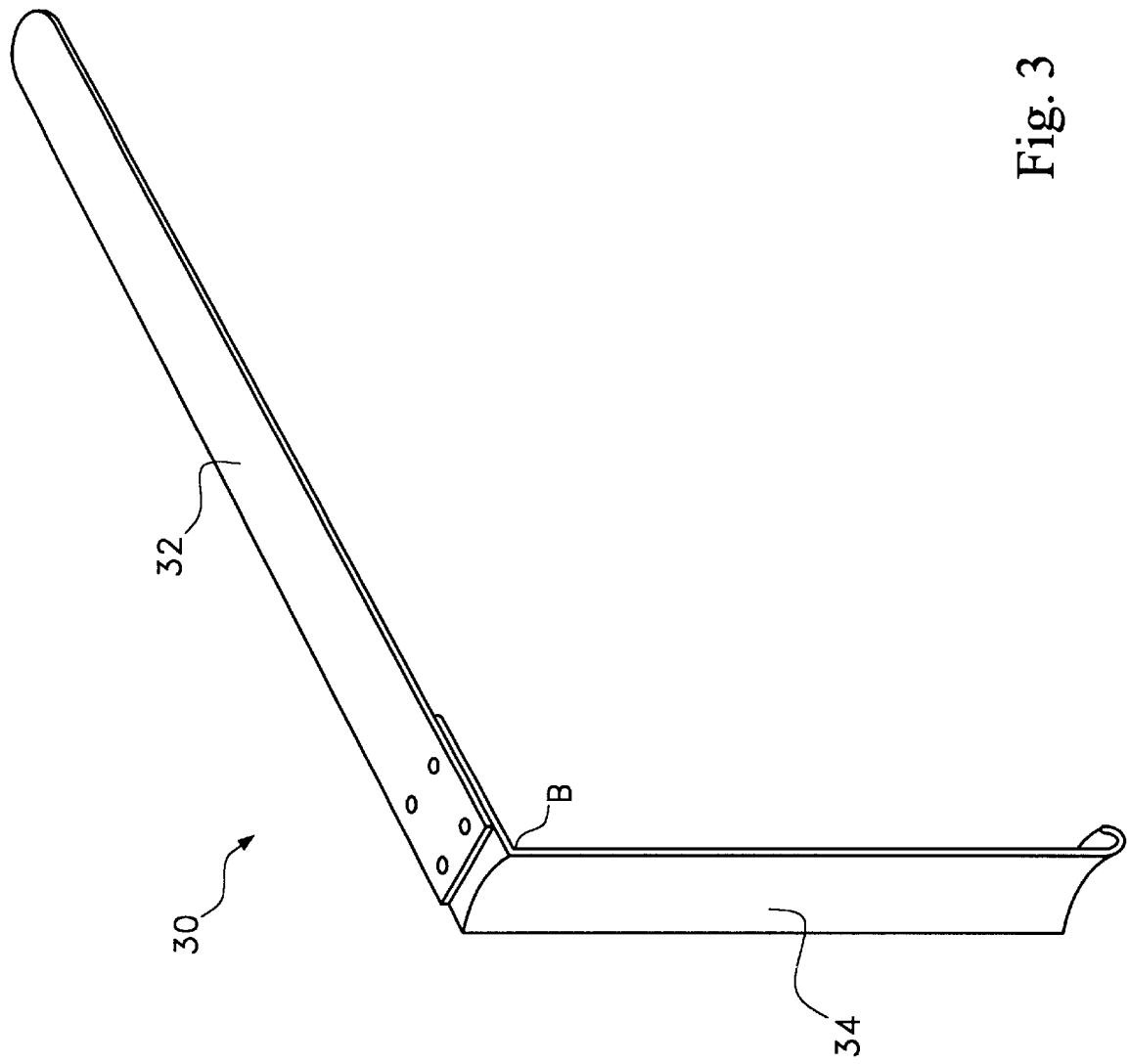
FIG. 3 is a perspective view of a second exemplary embodiment of a surgical retractor in accordance with the present invention.

Referring to FIG. 3, an alternate embodiment of a retractor 30 is shown in accordance with the present invention. The retractor 30 has a rigid metal blade element 34. However, the material of the rigid metal blade element 34 is angled at a perpendicular and also extends into part of the retractor's handle. Thus, the material of the retractor 30 on either side of the perpendicular bend B is made from rigid metal, such as stainless steel. As a result, any stresses that are concentrated at the perpendicular bend B during the use of the retractor 30 are experienced by the rigid stainless steel material.

The rigid material extending into the handle section of the retractor 30 joins to a malleable handle element 32. As such, the handle element 32 can be selectively bent by a surgeon, while the blade element 34 and the perpendicular bend B remain at a prefabricated orientation. More tensile force can therefore be applied to the embodiment of FIG. 3 than with the embodiment of FIG. 1, without concern of deforming the material at the perpendicular bend of the retractor.

Figure 4:
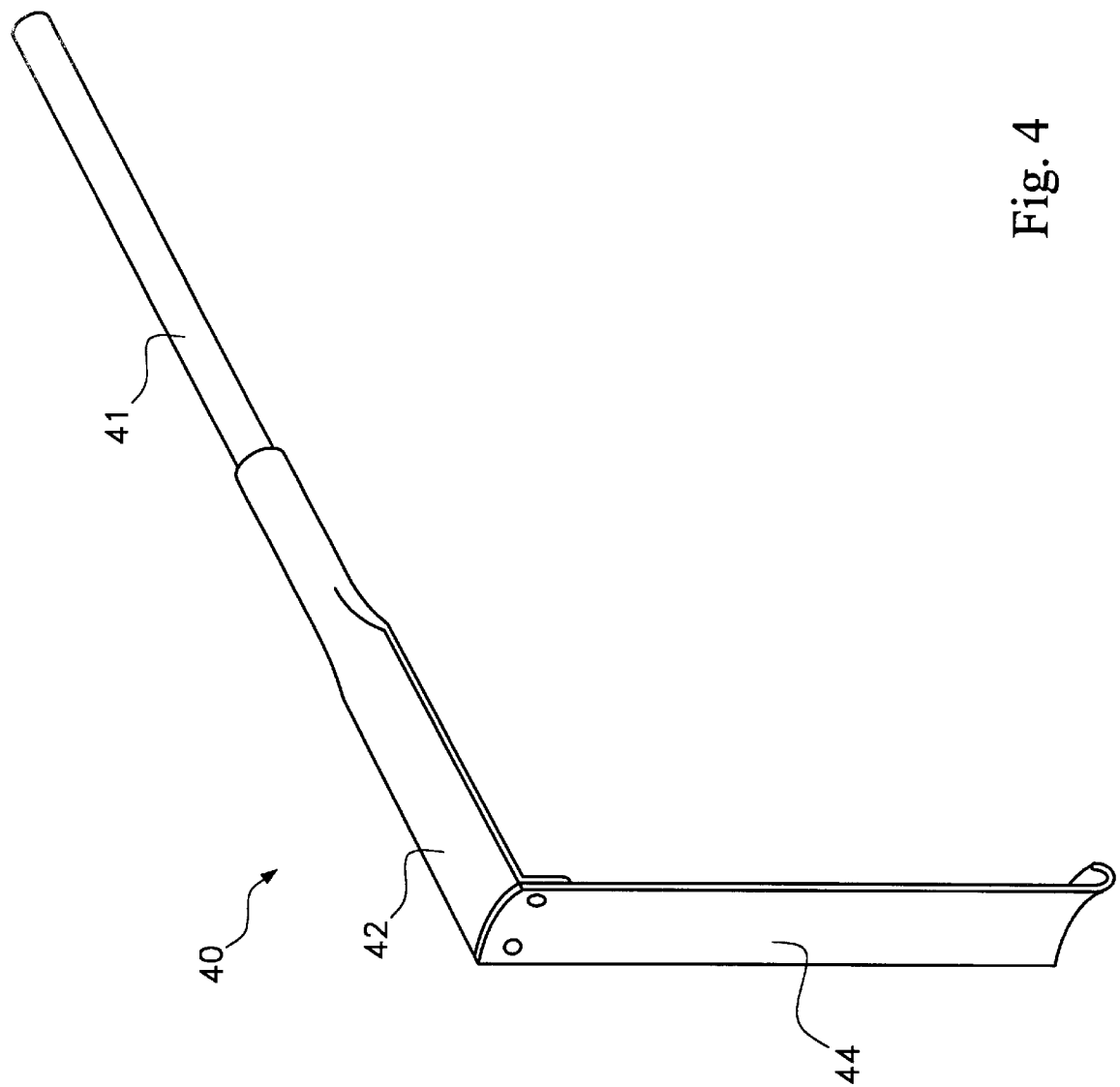
FIG. 4 is a perspective view of a third exemplary embodiment of a surgical retractor in accordance with the present invention.

In the embodiments of the retractor shown in FIG. 1 and FIG. 3, the retractors were simple hand held retractors. Retractors, however, are sometimes used as part of larger assemblies, wherein retractors are mounted to supporting frames. In this manner, a surgeon does not have to occupy one of his/her hands holding the retractor in position during a surgical procedure. Referring to FIG. 4, an embodiment of a retractor 40 is illustrated for use in such a circumstance. In FIG. 4, a rigid mounting rod 41 extends into the handle of the retractor 40. The mounting rod 41 is the element that is received and retained by some supporting frame. Retractors that terminate with rigid mounting rods have long been in use. What is unique about the embodiment shown in FIG. 4, is the use of a section of malleable material 42 between the mounting rod 41 and the rigid blade element 44. The presence of the section of malleable material 42 enables the relative orientation of the rigid blade element 44 and the mounting rod 41 to be selectively adjusted by a surgeon.

To use the retractor 40 shown in FIG. 4, a doctor sets a support frame near the body of a patient. During an operation, a surgeon bends the malleable section 42 on the handle of the retractor 40, so as to properly orient the blade element 44 of the retractor 40. The mounting rod 41 extending from the retractor 40 is then joined to the support frame. If the retractor 40 needs to be adjusted, the support frame need not be touched. Rather, the malleable section 42 of the retractor 40 can be deformed, thereby making the needed adjustment.

In the operating room, it is not uncommon for a surgeon's hands to become slick with blood. It is for this reason that certain surgical instruments are terminated with contoured handles that make the instruments easier to hold. Many surgical instruments are manufactured with a modular construction so that a single handle can be selectively attached to a plurality of different surgical instruments, as those instruments are used during an operation.

Figure 5:
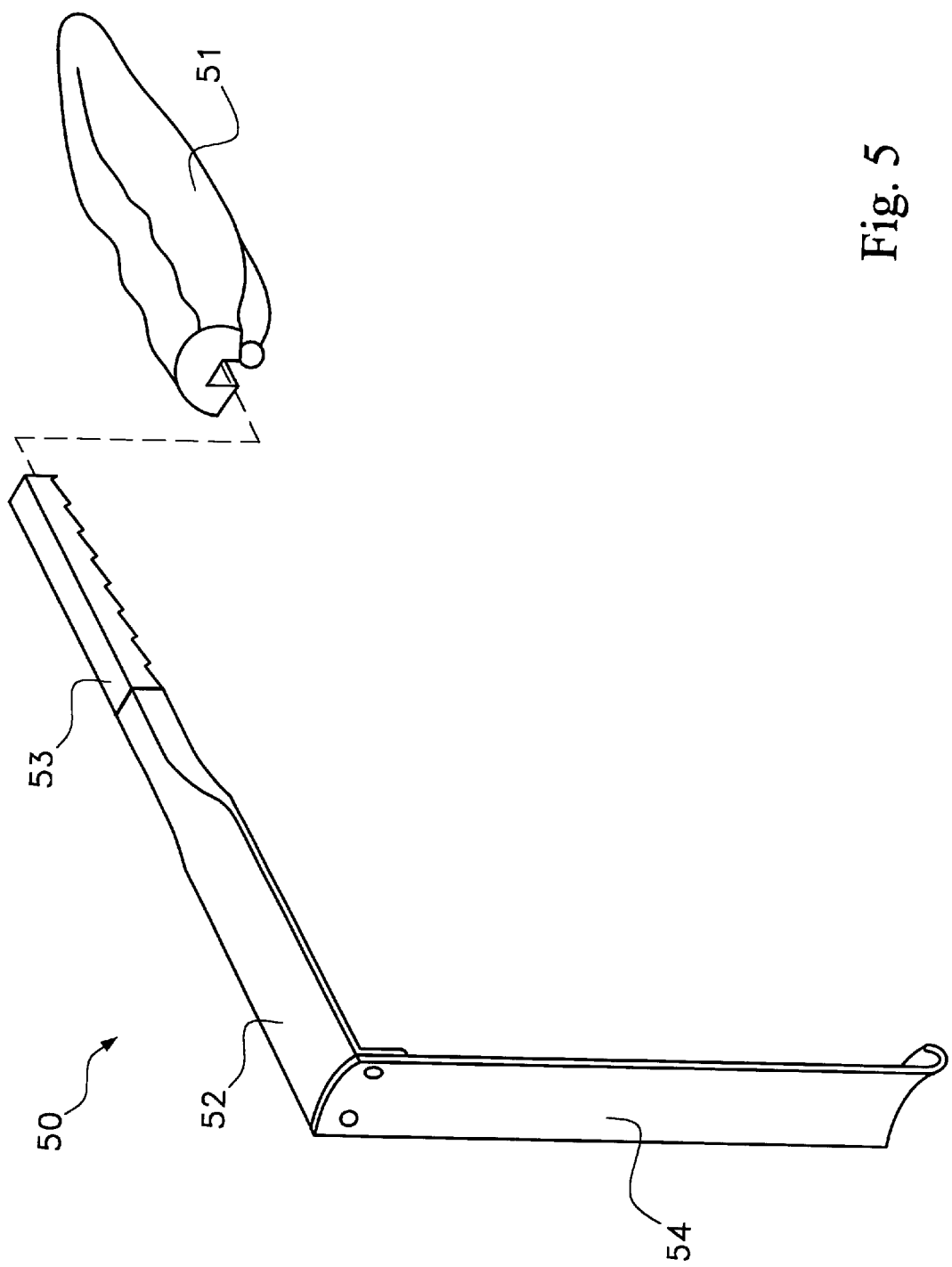
FIG. 5 is a perspective view of a fourth exemplary embodiment of a surgical retractor in accordance with the present invention.

Referring to FIG. 5, a retractor 50 is shown that is designed to be received by a modular handle 51. In the shown embodiment, a rigid attachment bar 53 extends from the retractor 50 and is received by the modular handle 51. The attachment bar 53 and handle design shown, are what is commonly called a Brookwalter handle in the field of surgery. The attachment bar 53 is the element that is received and retained by the-modular handle 51. Retractors that terminate with such mounting handles have long been in use. What is unique about the embodiment shown in FIG. 5, is the use of a section of malleable material 52 between the attachment bar 53 and the rigid blade element 54. The presence of the section of malleable material 52 enables the relative orientation of the rigid blade element 54 and the attachment bar 53 to be selectively adjusted by a surgeon.

To use the retractor shown in FIG. 5, a doctor attaches the modular handle 51 to the attachment bar 53. During an operation, a surgeon bends the malleable section 52 on the retractor 50, so as to properly orient the blade element 54 of the retractor relative the modular handle 51.

It will be understood that the embodiments of the present invention described and illustrated herein are merely exemplary and a person skilled in the art can make many variations to the embodiments shown without departing from the scope of the present invention. It should also be understood that the various elements from different embodiments can be mixed together to create alternate embodiments that are not specifically described. All such variations, modifications and alternate embodiments are intended to be included within the scope of the present invention as defined by the appended claims.

What is claimed is:

1. A retractor device, comprising:

a handle element having a first end, a second end, a first rigid section proximate said first end and a second rigid section proximate said second end, and a section of malleable material present in said handle element between said first rigid section and said second rigid section, wherein said malleable material enables the relative position between said first end and said second end to be selectively adjusted by hand;

a rigid retractor blade extending from said first end of said handle element.

2. The device according to claim 1, wherein said retractor blade has a semi-cylindrical shape.

3. The device according to claim 1, wherein said retractor blade extends from said first end of said handle element generally at a right angle.

4. The device according to claim 1, wherein said first rigid section is fabricated from the same rigid metal as said retractor blade.

5. A retractor, comprising:

a rigid blade element;

a handle element extending from said blade element, said handle containing a first end that is attached to said rigid blade, a rigid section and a malleable section disposed between said rigid section and said first end, wherein said malleable section can be deformed by hand.

6. The device according to claim 5, wherein said rigid section includes a rigid rod mounting.

7. The device according to claim 5, further including a contoured handle, wherein said contoured handle selectively interconnects with said rigid section.

8. The retractor according to claim 5, further including a mounting bar coupled to said rigid section of said handle element.

9. A method of orienting a surgical retractor, comprising the steps of:

providing a retractor having a rigid blade and a handle element extending from said blade, wherein said handle element contains at least one section fabricated from a malleable material that can be manually deformed;

deforming said at least one section of said handle element fabricated from malleable material, thereby selectively altering the shape of said handle element; and attaching a secondary handle to said handle element.

* * * * *